United States Patent [19]

Bacha et al.

[11] 3,978,117

[45] Aug. 31, 1976

[54] PROCESS FOR CONVERTING STYRENE BOTTOMS TO NITROBENZOIC ACIDS

[75] Inventors: John D. Bacha; Anatoli Onopchenko, both of Monroeville; Johann G. D. Schulz, Pittsburgh, all of Pa.

[73] Assignee: Gulf Research & Development Company, Pittsburgh, Pa.

[22] Filed: July 11, 1975

[21] Appl. No.: 595,158

[52] U.S. Cl............................................. 260/523 R
[51] Int. Cl.².......................................... C07C 51/33
[58] Field of Search...................... 260/523 R, 524 N

[56] References Cited
OTHER PUBLICATIONS

Fortina et al., "Chemical Abstracts" vol. 53 (1959) p. 17928a.

*Primary Examiner*—James O. Thomas, Jr.
*Assistant Examiner*—A. Siegel

[57] ABSTRACT

A process for converting styrene bottoms to nitrobenzoic acids, particularly para-nitrobenzoic acid, which involves nitrating styrene bottoms and then oxidizng the nitrated styrene bottoms.

6 Claims, No Drawings

PROCESS FOR CONVERTING STYRENE BOTTOMS TO NITROBENZOIC ACIDS

BACKGROUND OF THE INVENTION

1. Field of the Invention

This invention relates to a process for converting styrene bottoms to nitrobenzoic acids, particularly paranitrobenzoic acid, by subjecting the styrene bottoms to nitration and then subjecting the nitrated styrene bottoms to oxidation.

2. Description of the Prior Art

When ethylbenzene is subjected to dehydrogenation at elevated temperatures to obtain styrene, a heavy residue is obtained containing a multiplicity of compounds. This residue has limited commercial attraction, for example, in that it can be oxidized to obtain small amounts of benzoic acid, but in many cases its main utility is as fuel value.

SUMMARY OF THE INVENTION

We have found that such styrene residues can be converted in high yield to a product predominating in nitrobenzoic acid, particularly para-nitrobenzoic acid, by a process which comprises nitrating the residue with concentrated nitric acid and then subjecting the nitrated residue to oxidation with dilute nitric acid.

Any such residues obtained as a result of the dehydrogenation of ethylbenzene to obtain styrene can be used as charge herein. These dehydrogenation reactions can be carried out, for example, by passing ethylbenzene and excess steam (for example, about 1.0 to about 2.0 parts by weight of steam per part by weight of ethyl benzene) over a conventional, commercially available dehydrogenation catalyst, such as one containing 89 weight per cent iron oxide as $Fe_2O_3$, 2 weight per cent chromium oxide as $Cr_2O_3$ and 9 weight per cent $K_2CO_3$ 85 weight per cent $Fe_2O_3$, 2.0 weight per cent $Cr_2O_3$ 12.0 weight per cent KOH and 1.0 weight per cent NaOH; 72.4 weight per cent MgO, 18.4 weight per cent $Fe_2O_3$, 4.6 weight per cent CaO and 4.6 weight per cent $K_2O$; 83.1 weight per cent ZnO, 3.2 weight per cent $Al_2O_3$, 5.0 weight per cent CaO, 2.9 weight per cent KOH, 2.9 weight per cent $K_2SO_4$, and 2.9 weight per cent $K_2CrO_4$; 77.5 weight per cent ZnO, 7.5 weight per cent $Al_2O_3$, 4.7 weight per cent CaO, 4.7 weight per cent MgO, 2.8 weight per cent $K_2SO_4$, and 2.8 weight per cent $K_2CrO_4$; etc. at a temperature of about 550° to about 650° C. and atmospheric pressure using an ethylbenzene liquid hourly space velocity of about 0.2 to about 2.0. The product stream is quenched to a temperature of about 100° to about 200° C. and then transferred, together with a known or conventional free radical polymerization inhibitor, such as phenols, cresols, catechols, copper II salts, amines, such as aniline, quinone, para-quinonoxime, oximes, elemental sulfur or selenium, arsenic sulfide, etc., to a distillation column wherein the desired styrene is recovered. The free radical polymerization inhibitor inhibits the polymerization of styrene during the distillation. As a result of such distillation, the low-boiling components in the dehydrogenated product, such as by-product benzene and toluene and unreacted ethylbenzene are taken off, followed by the desired styrene. The residue, defined hereinafter as "styrene bottoms," is left behind in the distillation tower and constitutes the charge to the process defined herein. The styrene bottoms are believed to contain a large number of compounds, for example, upwards of 50 compounds. While many of the compounds present in the styrene bottoms have not been identified, and may include condensation, polymerization and decomposition products of the reactants and of the products formed during reaction, it is known that aromatic compounds such as small amounts of lighter components, for example, styrene, and heavy components, such as low molecular weight polymerized styrenes (oligostyrenes), diphenyl, naphthalenes, phenanthrene, stilbenes and polyethylbenzenes, bibenzyl, etc. are present. It is believed that substantially all of the products in the styrene bottoms are compounds based upon one or more aromatic rings.

The styrene bottoms defined above are subjected to nitration in a manner such that no more than one nitro group is placed on an individual aromatic ring. This can be done following conventional nitration procedures. For example, to an aqueous nitric acid solution having a concentration of about 40 to about 95 weight per cent, preferably about 70 to about 90 weight per cent, there is added, while stirring, the defined styrene bottoms charge. The amount of nitric acid needed is that amount sufficient to place one nitro group on each of the rings of the aromatic compounds in the styrene bottom charge and to maintain the resultant nitrated product obtained in solution. In general, about three to about 10, preferably about 3 to about 5, parts by weight of nitric acid, as 100 per cent nitric acid, is sufficient to effect such purposes. The temperature during nitration can vary over a wide range, for example, from about −20° to about 100° C., preferably from about −10° to about 60° C. Pressure does not affect the course of the reaction and pressures up to about 100 pounds per square inch gauge (about seven kilograms per square centimeter), or even higher, can be used, but in general atmospheric pressure is sufficient. The time required for nitration can also vary over a wide range, for example, from about 15 minutes to about 12 hours, but, in general, a period of about ½ hour to about two hours is sufficient. In order to facilitate the nitration reaction, conventional dehydrating agents, such as sulfuric acid or acetic anhydride, can be present, for example, in an amount that can be in the range of about 10 to about 300, preferably about 20 to about 100, weight per cent, based on the weight of the nitric acid.

The nitrated styrene bottoms product obtained above is then subjected to conventional nitric acid oxidation to obtain the desired product predominating in para-nitrobenzoic acid. If the nitration procedure defined above has been carried out in the presence of a dehydrating agent, as described, the dehydrating agent is first removed from the nitrated product before oxidation, since the presence of the dehydrating agent during oxidation can interfere with the smooth operation of the oxidation reaction. Thus, at the relatively high temperatures used during oxidation, the nitric acid will tend to oxidize the acetic anhydride, thus consuming valuable nitric acid and forming undesirable compounds, and the sulfuric acid will tend to sulfonate the nitrated styrene bottoms and can react with metal walls of the reactor. Removal of the dehydrating agent can be effected in any conventional manner. For example, this can be done by diluting the nitrated reaction mixture at room temperature with a large amount of water at room temperature and then recovering the precipitated nitrated styrene bottoms by filtration. The recovered nitrated styrene bottoms can then be subjected to oxidation with fresh nitric acid as described hereinafter. If no dehydrating agent has been used, the nitrated styrene bottoms can also be similarly recovered and subjected to oxidation, as described hereinafter, or, preferably, the total nitrated styrene bottoms are diluted with sufficient water to obtain a nitric acid concentration sufficient for oxidation and then the resultant mixture is subjected to oxidation, is described hereinafter.

The nitric acid oxidation of the nitrated styrene bottoms can be effected, for example, by oxidizing the same, while stirring, with aqueous nitric acid having a concentration of about five to about 50 weight per cent, preferably about 10 to about 40 weight per cent. The amount of nitric acid, as 100 per cent nitric acid, used can vary over a wide range, but, in general, at least about one part by weight of nitric acid, preferably about 2.5 to about 5.0 parts by weight of nitric acid, per part by weight of nitrated styrene bottoms is sufficient. The temperature during the reaction can be in the range of about 160° to about 220° C., preferably about 170° to about 190° C. Pressure seems to have no appreciable effect on the course of the reaction. In general a pressure of about 200 to about 500 pounds per square inch gauge (about 14 to about 35 kilograms per square centimeter), preferably about 250 to about 400 pounds per square inch gauge (about 17.6 to about 28 kilograms per square centimeter) is sufficient. A reaction period of about ½ to about 12 hours, preferably about one to about 4 hours, will suffice. As a result of such oxidation, a reaction product predominating in para-nitrobenzoic acid is obtained containing lesser amounts of ortho-and meta-nitrobenzoic acids.

The recovery of the nitrobenzoic acids from the oxidation can be effected in any convenient or conventional manner. For example, the reaction mixture is cooled to room temperature and then depressured and subjected to filtration to recover a first, or major, crop of nitrobenzoic acids. To recover the remainder of the nitrobenzoic acids the filtrate can be evaporated to dryness, dissolved in sodium hydroxide solution and filtered to remove a sodium hydroxide insoluble sludge. The filtrate, which is essentially the sodium salts of nitrobenzoic acids, is acidified with HCl and evaporated to dryness to produce sodium chloride and nitrobenzoic acids. Separation of the two from each other can be effected by extraction with a solvent, such as acetone to obtain a solution containing the nitrobenzoic acid. The sodium chloride is discarded and the solution is evaporated to dryness to obtain the second crop of nitrobenzoic acids. If desired, the nitrobenzoic acid mixture obtained can be treated in any conventional manner to separate and recover the individual isomers therein, for example, as in British Pat. No. 1,068,535. For some applications the total mixture of nitrobenzoic acids can be used as such, without separating into its individual isomers, for example, as plant growth inhibitors, antiviral agents, etc. If desired, the nitrobenzoic acids herein can be converted to the corresponding aminobenzoic acids in any conventional manner, for example, by following the procedures disclosed in U.S. Pat. Nos. 2,947,781 and 3,324,175.

DESCRIPTION OF PREFERRED EMBODIMENTS

A number of runs were carried out wherein styrene bottoms were added slowly, with stirring, to concentrated nitric acid to obtain nitrated styrene bottoms. In one run the nitric acid used was in admixture with sulfuric acid. In each run, except the last, the total nitrated product was diluted with water to obtain a desired nitric acid concentration therein and oxidation, while stirring, of the nitrated styrene bottoms product was effected. In the run wherein sulfuric acid was also present during nitration, the nitrated product was diluted with water, the solid nitrated product recovered by filtration and then combined with fresh nitric acid for the oxidation. The oxidation product obtained was cooled to room temperature and then depressured. Filtration of the product resulted in the recovery of a first crop of nitrobenzoic acid and treatment of the filtrate in the manner defined above resulted in the recovery of a second crop of nitrobenzoic acids.

The styrene bottoms used as charge in the first run was chemically analyzed and was found to contain 91.69 weight per cent carbon and 8.31 weight per cent hydrogen. Analysis by NMR showed 67.6 weight per cent of aromatic protons, 6.2 weight per cent olefinic protons and 26.1 alkyl group protons. GLC analysis indicated a complex mixture of hydrocarbons, fifty being visible components on the chromatogram, ten of which are major. The visible portion accounts for about one-half of the sample, with the remainder assumed to be high-boiling materials which did not elute off the chromatographic column. Each of the remaining styrene bottoms charge used herein were also submitted to NMR analysis and the results were found to correspond reasonably close to those of the first run identified above.

The styrene bottoms used in the runs herein was the residue obtained as a result of passing about one part by weight of ethylbenzene together with about 1.5 parts by weight of steam over a conventional dehydrogenation catalyst at an average temperature of 600° C. and atmospheric pressure at a liquid ethylbenzene hourly space velocity of about 0.5, quenching the resulting mixture to atmospheric temperature, adding a free radical polymerization inhibitor thereto and distilling to remove overhead low-boiling by-products, such as benzene and toluene, and unreacted ethylbenzene and the desired styrene.

The results obtained herein are tabulated below in Table I. Included also in Table I for reasons that will be apparent below, are data obtained by L. Fortina and R. Passerini in *Boll. Sci. fac. chim. ind. Bologna*, 17, 1–4 (1959), reported in *Chemical Abstracts*, 53, 17928a (1959).

TABLE I

| Charge | Run No. | | | | | | | | | Fortina Et Al Runs | |
|---|---|---|---|---|---|---|---|---|---|---|---|
| | I | II | III | IV | V | VI | VII | VIII | IX | | |
| Substrate | |←————————————————Styrene Bottoms————————————————→| | | | | | | | | |
| | | | | | | | | | | Liquid Portion | Semi-Solid Portion |
| Weight in Grams | 30 | 30 | 30 | 30 | 30 | 30 | 30 | 30 | 30 | 25.7 | 22.2 |
| Reaction Conditions | | | | | | | | | | | |
| Nitration | | | | | | | | | | | |
| HNO₃ Concentration | 90 | 90 | 90 | 90 | 90 | 90 | 90 | 70 | 70 | — | — |

TABLE I-continued

| Charge | Run No. I | II | III | IV | V | VI | VII | VIII | IX | Fortina Et Al Runs | |
|---|---|---|---|---|---|---|---|---|---|---|---|
| Weight of $HNO_3$ (As 100 Per Cent $HNO_3$), Grams | 202 | 162 | 224 | 224 | 224 | 295 | 164 | 140 | 196 | — | — |
| Temperature, °C. | 25 | 25 | 25 | 25 | 25 | 25 | 25 | 75 | 40 | — | — |
| Pressure, Pounds Per Square Inch Gauge | |←|  |  | Atmospheric |  |  |  |→| | — | — |
| Reaction Time, Hours | 1 | 1 | 1 | 1 | 1 | 1 | 2 | 6 | 3 | — | — |
| Oxidation | | | | | | | | | | | |
| $HNO_3$ Concentration | 35 | 32 | 40 | 39 | 40 | 48 | 27 | 38 | 38 | 20 | 30 |
| Weight of $HNO_3$ (As 100 Per Cent $HNO_3$), Grams | 140 | 114 | 159 | 158 | 160 | 223 | 114 | 118 | 171 | 50.5 | 44.4 |
| Temperature, °C. | 180 | 180 | 180 | 180 | 180 | 180 | 180 | 180 | 180 | 184 | 236 |
| Pressure, Pounds Per Square Inch Gauge | 330 | 300 | 300 | 300 | 300 | 300 | 300 | 300 | 300 | 720 | 750 |
| (Kilograms Per Square Centimeter) | (25) | (21) | (21) | (21) | (21) | (21) | (21) | (21) | (21) | (51) | (57) |
| Reaction Time, Hours | 1 | 1 | 1 | 1 | 1 | 1 | 1 | 1 | 1 | 1 | — |
| Yield Data | | | | | | | | | | | |
| Product Obtained | |←|  |  | Nitrobenzoic Acid |  |  |  |→| |←Benzoic Acid→| |
| Weight of Product, Grams | 37.5 | 41.1 | 39.3 | 36.6 | 41.9 | 42.6 | 40.1 | 32.2 | 33.9 | 3.03 | 2.67 |
| Yield, Per Cent | 77.8 | 85 | 81 | 76 | 87 | 88 | 82 | 66 | 70 | 12.8 | 12.0 |

In the above Table in Run No. IX there was also present in the nitration stage 276 grams of 96 per cent aqueous sulfuric acid as a dehydrating agent. In Run No. 1 86 weight per cent of the product was para-nitrobenzoic acid, 13 weight per cent metanitrobenzoic acid and 1 weight per cent was ortho-nitrobenzoic acid. The products of Runs Nos. II to VI were combined and analyzed to find 82 weight per cent para-nitrobenzoic acid, 14.8 weight per cent meta-nitrobenzoic acid and 3.2 weight per cent ortho-nitrobenzoic acid. The product in Run No. VII contained 84.5 weight per cent para-nitrobenzoic acid, 14.5 weight per cent metanitrobenzoic acid and 1 weight per cent orthobenzoic acid. In Run No. VIII the product was found to contain 77 weight per cent paranitrobenzoic acid and 20 weight per cent benzoic acid. This is believed to be the result of the reduced nitration during the nitration stage. Longer nitration would have resulted in greater nitration and the formation of less benzoic acid in the second stage. In Run No. IX only the first crop was analyzed and found to contain 95 weight per cent para-nitrobenzoic acid. For purposes of calculating yields in the above Table, it is assumed that the average structure in the styrene bottoms is a multiple of the styrene molecule. On this basis, each styrene unit is capable of producing one unit of the corresponding benzoic acid. Yield is thus determined by multiplying the weight of the styrene bottoms charge by the molecular weight of the benzoic acid expected divided by the molecular weight of the styrene bottoms unit. This corresponds to the theoretical yield. Thus, in Run No. 1, $$\frac{30 \times 167}{104} = 48.5 \text{ grams theoretical yield.}$$

Actual yield would then be $$\frac{37.5}{48.5} \times 100 = 77.8 \text{ per cent.}$$

The results obtained above are most unusual. As noted above, the results obtained by Fortina et al. when they subjected styrene bottoms, separated into two portions, to nitric acid oxidation are also included in Table I for comparison. Note that using conventional nitric acid oxidation conditions, as in the present case, Fortina et al obtain a yield of benzoic acid of but about 12 to about 13 per cent. Accordingly, it might be argued that had the styrene bottoms been nitrated prior to oxidation, a nitrobenzoic acid might be obtained instead of the benzoic acid obtained by Fortina et al the yield of nitrobenzoic acid, nevertheless, would be on the same order of magnitude. Note, however, that in the process defined and claimed herein a yield of nitrobenzoic acid of from about 66 to 88 per cent is obtained, which is at least about 5 times more than expected.

The process defined herein not only results in the production of a large amount of nitrobenzoic acids from styrene bottoms, but also results in the production of predominent amounts of the desired para isomer thereof. If one were to take the benzoic acid produced by Fortina et al from styrene bottoms and were to nitrate the same, not only would he obtain a correspondingly small amount of nitrobenzoic acid, as shown far lower than would be obtained herein, but the isomer produced would be the less desirable meta isomer, since it is well known that a carboxyl group on an aromatic ring is a meta directing group toward electrophilic substitution.

The nitrobenzoic acids produced herein are old and well known and have many utilities. Thus, they can be used as bacteriostatic agents as anti-viral agents and as plant growth inhibitors. Para-nitrobenzoic acid is particularly attractive, since it can be hydrogenated, using conventional means, to obtain para-aminobenzoic acid. The latter can be homopolymerized to give polyamides having high tensile strength and high temperature stability (Encyclopaedia of Polymer Science and Technology, Volume 10, pages 347 to 460, 1972, Interscience Publishers, N. Y.) or can be copolymerized with diphenylamines or terephthalic acids to obtain linear polymers suitable for use as fibers (U.S. Pat. Nos. 3,817,941 and 3,819,587).

Obviously, many modifications and variations of the invention, as hereinabove set forth, can be made without departing from the spirit and scope thereof, and therefore only such limitations should be imposed as are indicated in the appended claims.

We claim:

1. A process for converting styrene bottoms to a product predominating in para-nitrobenzoic acid which comprises nitrating said bottoms with nitric acid and then oxidizing the nitrated product with nitric acid, said nitration being conducted with an aqueous nitric acid solution having a concentration of about 40 to about 95 weight per cent at a temperature of about −20° to about 100° C. over a period of about 15 minutes to about 12 hours and said oxidation being conducted with an aqueous nitric acid solution having a concentration of about five to about 50 weight per cent at a temperature of about 160° to about 220° C. for about one-half to about 12 hours.

2. The process of claim 1 wherein said styrene bottoms comprise the residue remaining from the process wherein ethylbenzene is subjected to dehydrogenation to obtain styrene.

3. The process of claim 1 wherein the nitric acid concentration during nitration is in the range of about 70 to about 90 per cent.

4. The process of claim 1 wherein the temperature during nitration is in the range of about −10° to about 60° C.

5. The process of claim 1 wherein the nitric acid concentration during oxidation is in the range of about 10 to about 40 per cent.

6. The process of claim 1 wherein the temperature during oxidation is in the range of about 170° to about 190° C.

* * * * *